(12) United States Patent
Williams

(10) Patent No.: US 8,463,344 B2
(45) Date of Patent: Jun. 11, 2013

(54) ANTIGEN MONITORING SYSTEM

(76) Inventor: Marlon Williams, Fort Lauderdale, FL (US)

( * ) Notice: Subject to any disclaimer, the term of this patent is extended or adjusted under 35 U.S.C. 154(b) by 1288 days.

(21) Appl. No.: 11/812,964

(22) Filed: Jun. 22, 2007

(65) Prior Publication Data

US 2008/0319289 A1 Dec. 25, 2008

(51) Int. Cl.
*A61B 5/1455* (2006.01)
(52) U.S. Cl.
USPC .......................................... 600/322; 600/310
(58) Field of Classification Search
USPC ........................................ 600/310, 322, 473
See application file for complete search history.

(56) References Cited

U.S. PATENT DOCUMENTS

| | | | | |
|---|---|---|---|---|
| 5,571,152 | A | * | 11/1996 | Chen et al. ...................... 607/92 |
| 6,122,536 | A | * | 9/2000 | Sun et al. ........................ 600/341 |
| 6,208,894 | B1 | * | 3/2001 | Schulman et al. ............. 600/300 |
| 6,398,710 | B1 | * | 6/2002 | Ishikawa et al. .............. 600/300 |
| 6,774,209 | B1 | * | 8/2004 | Rondon et al. ................ 530/300 |
| 7,228,160 | B2 | * | 6/2007 | Haight et al. .................. 600/316 |
| 7,318,903 | B2 | * | 1/2008 | Link et al. .......................... 216/2 |
| 2004/0018519 | A1 | | 1/2004 | Wright, Jr. |
| 2004/0078219 | A1 | * | 4/2004 | Kaylor et al. ................. 600/300 |
| 2004/0180391 | A1 | | 9/2004 | Gratzl et al. |
| 2005/0221276 | A1 | | 10/2005 | Rozakis et al. |
| 2005/0266045 | A1 | * | 12/2005 | Canham et al. ............... 424/423 |

* cited by examiner

*Primary Examiner* — Eric Winakur

(57) ABSTRACT

A method for detecting cancer in a subject includes administering polysilicon mirrors to the subject, transmitting near infrared light through subject's skin, receiving light which is reflected from the polysilicon mirrors though the subject's skin, converting received light into a digital signal and calculating a level of CEA in the subject's blood from the digital signal.

6 Claims, 3 Drawing Sheets

ANTIGEN MONITORING SYSTEM

FIELD OF THE INVENTION

The present invention relates to the wireless monitoring of antigen levels in blood, particularly in the blood of colorectal cancer patients. The present invention also relates to the monitoring of other cancers with antigen markers in blood, for example Ovarian/Cervix/Uterus-CA-125, Testicular-Alphafetaprotein, Gastrointestinal/Pancreas-CA19-9.

BACKGROUND OF THE INVENTION

Colorectal Cancer (i.e., cancer of the Colon, Rectum, Anus, Appendix) is the second leading cause of cancer deaths in the United States. Only lung cancer claims more lives. This year, more than 130,000 Americans will be diagnosed with colorectal cancer. Similar statistics are reported for many European countries. Certain types of cancer are associated with antigen markers in the blood, which holds a potential for early diagnosis by detection or monitoring of antigen levels. Examples of cancers and their associate antigen markers are: prostate cancer—PSA; pancreatic cancer—CA125; ovarian and uterine cancer—fetaprotein; breast and lung cancer—βdlh.

While cancer is generally more receptive to treatment if diagnosed in the early stages, it can be difficult to detect in an early stage. With the recent emergence of genetic expression profiling, oncologist have broken down malignancies to their genetic profile which will allow them to classify cancers into distinct categories. Tissues sampled for such genetic expression profiling can be studied for antigen markers associated with additional types of cancers.

Existing methods of detecting and monitoring cancer are time consuming and complex. For example, a patient must go to a facility, such as his physician's office, to have blood drawn. The blood is then sent to an on-site or off-site laboratory for processing to determine amounts of antigen markers. Costly equipment is generally required, and the overall process can take a great deal of time. The time-consuming nature of this process becomes particularly burdensome when a patient may return for testing periodically, such as weekly or monthly. Further, the invasive nature of blood tests is often a deterrent to patients.

A "biomaterial" is a non-living material used in a medical device which is intended to interact with biological systems. Such materials may be relatively "bioinert", "biocompatible", "bioactive" or "uresorbable", depending on their biological response in vivo.

When silicon is deliberately riddled with nanometer-sized holes, it becomes biocompatible and biodegradable, and will not be rejected by the body and it will dissolve harmlessly over time. Silicon chips have been implanted into the body before—for example in cochlear implants that convert sounds into electrical signals and feed them directly into the brain—but they had to be shielded from body tissues and the bloodstream.

Porous silicon, or "Biosilicon™", needs no such protection—its only by-product is silicic acid, which is present in many common foods and drinks. It can be crafted into orthopedic and electronic structures and perform a variety of medical functions inside the body automatically.

A Biosilicon implant could be crafted into temporary scaffolds or pins that would promote bone healing and growth and then dissolve into nothing. Alternatively, it could contain both a reservoir of drugs and a tiny computer system to control timing and dosage. It could even be used as an internal diagnostic device, transmitting data about a patient through his or her skin and enabling a doctor to fine-tune its drug-release program without the need for surgery.

SUMMARY OF THE INVENTION

It is an object of the invention to provide method and device of detecting the antigen level in a patient's blood stream.

According to an embodiment of the invention, a device for detecting cancer in a subject is provided. The device may include an infrared sensor for emitting near infrared light to penetrate the subject's skin. The device may further include an analog to digital converter for converting an analog signal from the infrared sensor to a digital signal. The device may also include a microcontroller to calculate a carcinoembryonic antigen (CEA) level in the subject's blood stream.

According to another embodiment of the invention, the device may further include a read-only memory for storing an output of the microcontroller.

According to yet another embodiment of the invention, the device may include a communication device for transmitting the output of the microcontroller stored in the read-only memory to another device. The communication device may be a cellular modem and may communicate with another device via the Internet.

According to an embodiment of the invention, the microcontroller may calculate a change in a CEA level in the subject's blood stream. According to a further embodiment, the infrared sensor may receive light reflected from polysilicon mirrors in the subject's blood.

According to another embodiment of the invention, a method for detecting cancer in a subject may include administering polysilicon mirrors to the subject, transmitting near infrared light through subject's skin, receiving light which is reflected from the polysilicon mirrors though the subject's skin, converting received light into a digital signal and calculating a level of CEA in the subject's blood from the digital signal.

DETAILED DESCRIPTION

Figure 1:
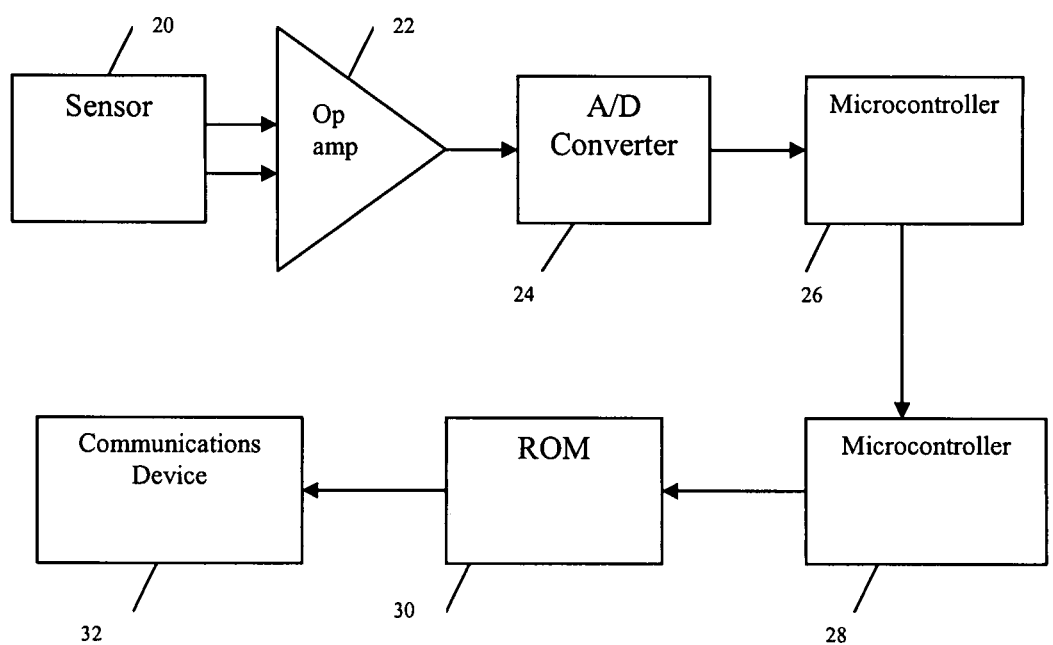
FIG. 1 illustrates an embodiment of a process utilizing the device and method of the present invention.

As stated above, cancerous tissues are being studied to identify antigen markers for many different types of cancers. As antigen markers are extracted from the tissue samples and identified, the present invention contemplates using them with a rule-based software to create the intelligence mechanism for use with an integrated circuit (referred to herein as an I3C) that merges digital technology with bioinformatics to formulate a non-invasive approach to cancer detection and management. In an embodiment of the invention, the rule-based software is interfaced with digital technology to alert a communication device such as a paging device, which the patient keeps close by. Alternatively, or additionally, the patient's physician or other care giver is notified through various known methods of communication, either wireless or wired.

In an embodiment of the invention, the communication device will be interfaced and equipped with a Wide Area Network (WAN) communication interface so that the patient is constantly within a global-positioned fixed communication loop. In such an embodiment, the only significant time that the patient will not be within this fixed loop is during flight or in certain overseas areas. In these cases, the patient is placed back in the loop when returning to WAN portals. The communication device would then alert a network database (for example via E-mail or Internet) at the physician or caregiver's office of a possible recurrence of a particular protein. In an alternative embodiment, the communication device utilizes known cellular communication technology (similar to text messaging) or known satellite communication technology.

According to an embodiment of the invention, the I3C is generally the size of a commercially available PDA to enhance portability and usability. Indeed, the present invention contemplates integrating the I3C into existing PDA-type or cell phone devices. The I3C comprises an integrated circuit including an application-specific integrated circuit (ASIC) and a light source. An ASIC is an integrated circuit customised for a particular use, rather than intended for general-purpose use. The I3C also comprises a transducer (with analog to digital conversion), two data acquisition microcontrollers for performing arithmetic functions and input/output, memory such as read only memory (ROM) for information and data storage, and a WAN interface for data transfer. When these electronic components are integrated into a device, the device allows a sensor (incorporated into the ASIC) to report an analog voltage proportional to a protein marker concentration to a transducer. The transducer will convert this voltage to a digital value. The memory receives the information and stores it along with the time and date, either in analog or digital form.

An exemplary embodiment of the invention discussed hereinafter works with the antigen marker carcinoembryonic antigen (CEA) in the patient's blood. It is to be understood, however, that the present invention contemplates detecting and monitoring a variety of antigen markers in a similar fashion as described below.

CEA is a lycoprotein involved in cell adhesion, and is normally produced during fetal development. The production of CEA stops before birth, and is therfore not usually present in the blood of healthy adults, although levels are raised in heavy smokers. CEA was first identified in 1965 by Phil Gold and Samuel O. Freedman in human colon cancer tissue extracts. It was found that serum from individuals with colorectal, gastric, pancreatic, lung, and breast carcinomas had higher levels of CEA than healthy individuals. CEA measurement is presently used to identify recurrences after surgical resection of cancerous cells. Elevated CEA levels should return to normal after surgical resection, and elevation of CEA during follow-up can therefore be an indicator of cancer recurrence. CEA levels may also be raised in some non-neoplastic conditions like ulcerative colitis, pancreatitis, and cirrhosis.

CEA and related genes make up the CEA family belonging to the immunoglobin superfamily. In humans, the carcinoembryonic antigen family consists of 29 genes, 18 of which are normally expressed.

The I3C receives inputs from multiple in vivo porous silicon mirrors (PSMs). The input includes at least one of a level of CEA in a patient's blood and a change in level of CEA in a patient's blood. PSMs are biodegradable surfaces that dissolve harmlessly over a period of time in the body. They elicit a specific biological response when in vivo, which results in formation of a bond with certain living tissue. PSMs comprise of particles of silicon etched with nano-scale patterns of pores making them extremely efficient light reflectors. Certain PSMs have been designed for early detection of initial incidence and recurrence of cancers. This is achieved by an application of a selective process of a tumor antibody such as CEA. In an embodiment of the invention, the PSM's are contained in a capsule swallowed by the patient. In another embodiment of the invention, immunoassays are placed into etchings of the PSMs, which are then implanted just below the skin. The implantable PSM is preferably approximately 5 mm wide and 0.5 mm thick. After implantation or other introduction into the patient's bloodstream, PSM particles having CEA-specific immunoassays bind to the CEA molecules. The porous silicon used in the PSMs is biocompatible and biodegradable, and therefore causes no side effects while in the body or after disintegration. Porous silicon differs from non-porous silicon because it has been treated under special acid conditions which make it porous. Once the silicon becomes porous, it acts like a highly reflective mirror. The PSMs eventually breakdown into silicic acid, which is said to be harmless to the body.

The I3C includes and monitors this process, or detects amounts of antigen markers in a patient's blood that bind to the PSMs, using a light source and an associated light sensor. According to an embodiment of the invention, the light source emits near infrared light. Near infrared light is used because it can penetrate the patient's skin to reach the PSMs. After the PSMs have reached the patient's bloodstream, the patient places a portion of his body, such as a finger, on the sensor and the light source is activated, causing the near infrared light to reach the etched surfaces of the PSM in the patient's blood to reflect the light. Intensity and/or other characteristics of light reflected from the PSMs will vary according to the amount of antigen markers in the patient's blood. This is because the antigen markers will adhere to the PSMs and interfere with light reflection, much in the same way that a layer of less reflective substance (such as Vaseline) placed on a mirror will alter the characteristics of ambient light from that mirror. The present invention contemplates using other types of light sources that can penetrate the dermis, paired with an appropriate sensor.

Studying the change in reflectance cause by differing concentrations of antigen marker in the blood identifies a formula ($\Delta x/\Delta t$) that allows calculation of the amount of antigen marker in a patient's blood, and therefore changes in the amount of antigen marker in the patient's blood.

As illustrated in the exemplary embodiment of FIG. 1, sensor 20, preferably a retroreflective photoelectric sensor, is provided. A photoelectric sensor is a device used to detect the presence of an object by using a light transmitter, in this case infrared, and a photoelectric receiver. A retroreflective photoelectric places the transmitter and receiver at the same location and uses a reflector to bounce the light beam back from the transmitter to the receiver. An object is sensed when the beam is interrupted and fails to reach the receiver. A proximity-sensing arrangement is one in which the transmitted radiation must reflect off of the object in order to reach the receiver. In this mode, an object is detected when the receiver sees the transmitted source rather than when it fails to see it. The output of the retro-reflective photoelectric sensor 20 is analog signal that represents the amount of antigen marker that has bound to the PSM. The sensor 20 will preferably emit up to 2.5 mm of near infrared light into the epidermis establishing a proportional relationship between antigen in blood and antigen on mirrors. The perpendicular refection then comes back to the collector side of the transistor. NPN phototransistor is used in this device because the intensity of the signal measurement out is perpendicular and will have a higher amplification and the NPN transistor collector allows for greater currents and faster more accurate operation.

The output of the sensor 20 in the input to an operation amplifier (op-amp) 22. The op-amp may perform signal conditioning of the fluctuations of the reflection due to individual patient epidermis differences. This is so that individual skin conditions do not mask the antigen levels on the signal measurement out. The op-amp will be programmed and set according to the reflection parameters of the porous silicon mirrors on the signal measurement out with no antigen in the blood and the lowest reflection with antigen in blood of a patient in remission. Since the I3C is preferably a CMOS (complimentary metal oxide semiconductor) circuit, the actual voltage of the reflection with no antigen in blood will be programmed in the op-amp as the input bias current. The lowest voltage of the reflection of a patient in remission will be programmed as the input offset voltage. The op-amp 22 may now use the input bias current and the input offset voltage against the incoming current (reflection) from the phototransistor to compensate for the common mode rejection ratio (CMRR). The CMRR will allow the op-amp 22 to toggle the reflection between the two inputs to find the common mode signal. In the event that the op-amp CMRR rejects the measurement (signal does not fall between the average of the 2 set parameters), the device may alert the patient to run the test again. This can compensate for the fluctuations of the individual patient epidermis differences so that skin conditions do not mask antigen levels on the signal measurement out.

The output of the op-amp 22 is fed to the analog to digital converter 24. The A/D converter 24 converts the buffered reflection from the op-amp from an analog signal to a digital signal. A proportional relationship between antigen concentration on the mirrors and the intensity of signal measurement out may be established. Analog perpendicular reflection was sent back to the collector of the phototransistor, transferred to an operational amplifier for buffering, and now has been sent to a transducer which has converted the reflection from a voltage to a digital number. This conversion process will be determined by a set of 256 preprogrammed discrete values which can be produced over a wide range of voltages. The transducer can be preprogrammed with an 8-bit resolution, meaning it can encode an analog input to 1 in 256 different levels. The values will range from 0-255 depending on the application.

Microcontrollers 26 and 28 enable the transfer of the newly converted digital information to two data acquisition microcontrollers for arithmetic functions which will determine the results of the test, i.e., the antigen level in the patient's blood stream. More specifically, the newly transferred value from the transducer, which represents the amount of antigen in the body at the present time, goes first to the address bus of the microcontroller for primary/temporary storage before being transferred to the control bus. The control bus can decode the value and convert the information to a binary coded decimal (BCD). The control bus may then transfer the binary coded value to the arithmetic logic unit (ALU). The ALU of this microcontroller will preferably be programmed to divide the BCD value by the number of days since last physician visit. The resulting numerical value, known as the slope of patient response (SOPR), is now transferred to the data bus. The data bus receives the SOPR and holds it in a RAM for the next set of instructions. Although two microprocessors and an operational amplifier have been described in conjunction with this embodiment, it should be understood that both arithmetic functions can be programmed into one microprocessor and the signal conditioning can be programmed into the transducer during the A-D conversion process.

The SOPR is transferred to the address bus of the second data acquisition microcontroller 28 for primary/temporary storage before being transferred to the control bus. The control bus takes the numerical SOPR value and decodes it into BCD before transferring it to the ALU. The ALU now has the SOPR in binary form. The ALU on this microcontroller will be programmed to divide the change in the BCD value (antigen level) by the change in time ($\Delta x/\Delta t$), also known as the DATD. The resulting numerical value, known as the discrete approximation of time differential, is now transferred to the data bus. The data bus receives the DATD and holds it in RAM for the next set of instructions.

Read-only memory (ROM) 30 stores the numerical DATD before being transferred to the parallel EEPROM for storage. Preferably, there will be 256 addressable memory locations programmed on this integrated circuit to cover the ample amounts of samples physicians may want. The DATD numerical value is transferred to the first set of address ports on the integrated circuit. The address bus then decodes the DATD back to BCD. The BCD is now transferred to the data bus and stored in the (ROM) 30 until further instruction. The ROM simply remembers what the outputs should be for any given 256 combinations of inputs.

Communication device 32 may be a wide area network 30 or other communication device which is capable of communication, preferably over the Internet. Once the information is transmitted to the Internet, it can be received by any party, such as the patient's doctor. Alternatively, the communication device may be a cellular modem which would dial a third party, such as the physician, and transmit the necessary information. As can be readily understood, there are many available means of communicating this information to a third party and this application is not intended to be limited to any one method.

In a preferred embodiment, the DATD stored BCD amounts are transferred via a cellular modem to a physician database for analysis. The physician can now receive in, an email format, the dates, times, and values of samples, for example. The physician now takes the sum total of all samples taken and divides it by the number of samples taken. The resulting numerical value is known as the "Patient Rate Of Change."

The measurement taken by the I3C can also be used to determine a discrete approximation of time differential, which measures the average antigen level over time.

For example, if a patient's antigen measurements for the past 12 months have been 4, 4, 4, 6, 7, 2, 5, 5, 5, 8, 9, 10, the average is the sum of these measurements (69) is be divided by the number of measurements (12) to get the an average antigen level of 5.75. In medical terms, the discrete approximation of time differential is referred to as a differential amount of CEA in time allotted. In an embodiment of the invention, the slope of patient response and the differential amount of CEA in time allotted are communicated to a physician or caretaker, for example via email or another suitable communication protocol as discussed above. A physician or caretaker receiving the information can determine whether the patient—s CEA level is low, moderate, or elevated (symptomatic of cancer recurrence).

Figure 2A:
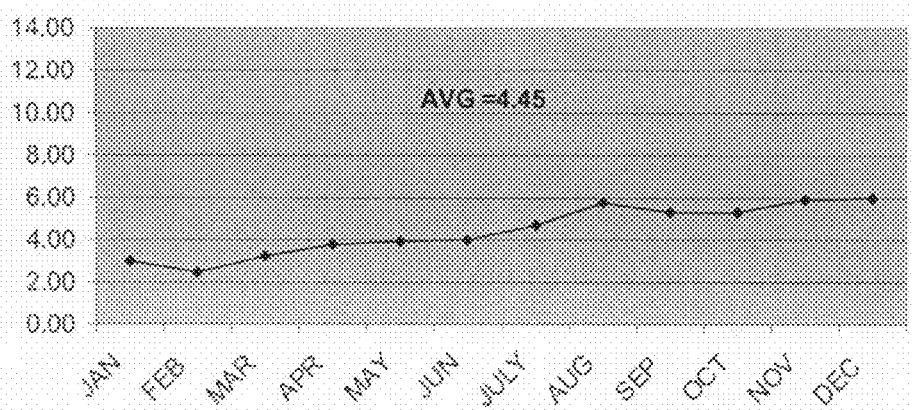
FIGS. 2A-2C graphically illustrate the measured values over a period of time.
Figure 2B:
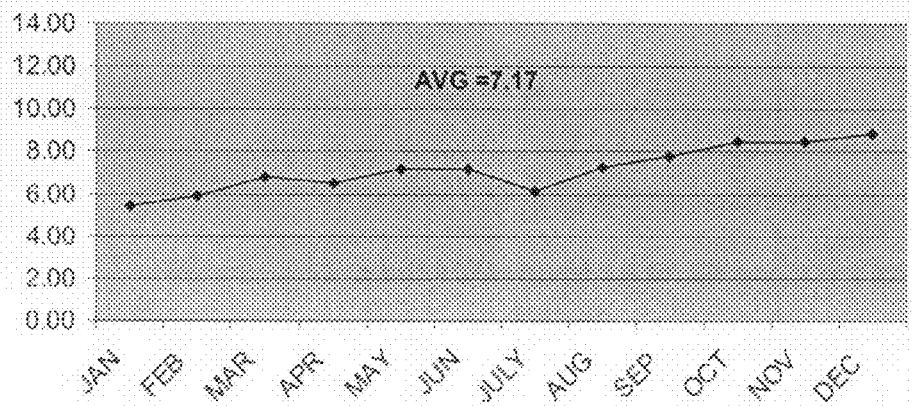
Figure 2C:
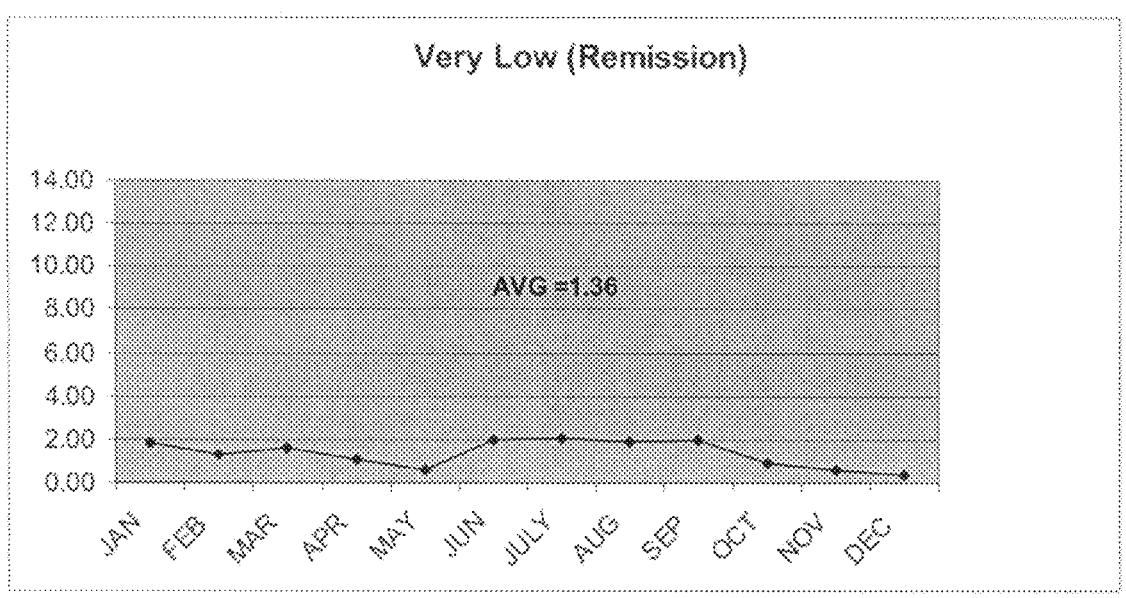

FIGS. 2A-2C show differences in levels of CEA relative to what each level means from a standpoint of recurrence and remission.

The entire disclosure of the patents and publications referred in this application, if any, are hereby incorporated herein in entirety by reference.

What is claimed is:

1. A method for detecting or monitoring cancer in a subject, comprising:
   administering polysilicon mirrors to random locations within the bloodstream of a subject orally or by injection;
   transmitting near infrared light through the subject's skin;
   detecting light which is reflected from the polysilicon mirrors though the subject's skin;
   converting received light into a digital signal; and
   calculating a level of CEA in the subject's blood from the digital signal.

2. The method of claim 1 wherein differences in the level of CEA in a subject's blood are determined based on previously stored measurements and currently taken measurements.

3. The method of claim 1 wherein the level of CEA is stored.

4. The method of claim 1 wherein the level of CEA is transmitted to a third party.

5. The method of claim 4 wherein the level of CEA is transmitted to the third party via an Internet.

6. The method of claim 1 wherein an intensity of light reflected from said polysilicon mirrors varies according to an amount of antigen markers in the subject's blood.

\* \* \* \* \*